United States Patent [19]

Ohyama

[11] Patent Number: 4,978,525

[45] Date of Patent: Dec. 18, 1990

[54] AGENTS FOR PREVENTING THE FORMATION OF GRAY HAIRS

[75] Inventor: Yasuaki Ohyama, Onojo, Japan

[73] Assignee: Sansho Seiyaku Co., Ltd., Fukuoka, Japan

[21] Appl. No.: 328,997

[22] Filed: Mar. 27, 1989

[30] Foreign Application Priority Data

Mar. 31, 1988 [JP] Japan .................................. 63-80536
May 13, 1988 [JP] Japan ................................ 63-117410

[51] Int. Cl.$^5$ .......................... A01K 7/06; A01K 7/13
[52] U.S. Cl. ............................................ 424/70; 8/405
[58] Field of Search ................. 424/70; 514/560, 549, 514/552; 8/405

[56] References Cited

FOREIGN PATENT DOCUMENTS 72717 4/1986 Japan ................................... 514/560

OTHER PUBLICATIONS

Grant & Hackh's Chemical Dictionary, 5th Ed., p. 610, 1987.

Primary Examiner—Ellis P. Robinson
Assistant Examiner—Susan S. Rucker
Attorney, Agent, or Firm—Jordan and Hamburg

[57] ABSTRACT

Agents highly effective in preventing hair from turning gray with no adverse effects upon skin or hair contain, as an active ingredient, an unsaturated fatty acid or an ester thereof represented by the following general formula:

A—COOR

[wherein A is a radical of $CH_2=CH(CH_2)_n$- or $CH_3(CH_2)_{10}CH=CH-(CH_2)_m$-, R is hydrogen atom or alkyl group having 1 or 2 carbon atoms, n is an integer 0 to 22, and m is an integer 5 or 6].

5 Claims, No Drawings

AGENTS FOR PREVENTING THE FORMATION OF GRAY HAIRS

BACKGROUND OF THE INVENTION

1. Field of the Invention

This invention relates to agents for preventing the formation of gray hairs by application to the skin, particularly, agents for preventing the formation of gray hairs which contain an unsaturated fatty acid as an active ingredient.

2. Description of the Prior Art

Gray hair is generally observed in elderly people. It impresses people with the depth of personal character owing to an advanced age. On the other hand, however, it gives an aged impression, and particularly the gray hairs of younger people are unfavorable in general. To hide gray hairs, many studies have been made on hair dyes and many products have been on the market. Hair dyes, however, give only temporary relief, and dyeing must be repeated with the growth of gray hairs. In addition, hair dyes of the oxidative type widely used at present tend to injure the skin by the action of oxidants involved.

Under these circumstances, many studies have been made on agents which substantially prevent the formation of gray hairs.

These include agents containing plant extracts as active ingredients, such as agents prepared from black sesame, leaves of Japanese black pines, and sea tangles (Japanese Patent Kokai No. 87515/1981); agents comprising extract of mustard leaves (Japanese Patent Kokai No. 79617/1981); agents comprising extract of Japanese green gentian (Japanese Patent Kokai No. 70605/1984); agents comprising extract of Acathopanax sieboldianus (Japanese Patent Kokai No. 178805/1985); and agents comprising extract of Angelica keiskei Koidzumi (Japanese Patent Kokai No. 77307/1987). Also disclosed are agents comprising pituitary hormone (Japanese Patent Kokai No. 63510/1987); agents comprising 3-(3,4-dihydroxyphenyl)-L-alanine (Japanese Patent Kokai No. 63509/1987); agents comprising C-AMP (cyclic adenosine 3',5'-monophosphate) (Japanese Patent Kokai No. 45527/1987); agents comprising vitamin D3 (Japanese Patent Kokai No. 174705/1985), and agents comprising minoxidyl (Japanese Patent Kokai Nos. 165310/1986 and 227518/1986).

The active ingredients used in these conventional agents are mainly plant and animal extracts, or animal components that participate in biological activities. Hence, there are some limitations upon the manufacture of these compounds, and their effects are inconsistent and not satisfactory.

SUMMARY OF THE INVENTION

The object of this invention is to provide a new agent containing, as an active ingredient, a substance of relatively simple structure which is easily available and has high activity to prevent the formation of gray hairs.

Melanin contained in hair is an important factor in determining its color tone. This substance is produced in melanocytes (pigment cells) in the upper part of hair root and absorbed by keratinocytes (hair cortical cells), and moves upward with the growth of hairs. Gray hair, which is a phenomenon of biological aging, results from a decrease in the number of melanocytes and depression of their functions.

In the course of basic research on the phenomenon of gray hair formation and its mechanism, the inventors have discovered that an unsaturated fatty acid having a double bond at a position apart from the carboxylic group is effective in activating melanin production by the pigment cells in an experiment using cultured pigment cells (B16 melanoma cells). This invention was accomplished on the basis of this finding.

Thus, this invention relates to agents for preventing the formation of gray hair which contain, as an active ingredient, an unsaturated fatty acid or an ester thereof represented by the following general formula:

$$A\text{—COOR} \qquad (1)$$

[wherein A is a radical of $CH_2=CH(CH_2)_n-$ or $CH_3(CH_2)_{10}CH=CH-(CH_2)_m-$, R is hydrogen atom or an alkyl group having 1 or 2 carbon atoms, n is an integer 0 to 22, and m is an integer 5 or 6].

DETAILED DESCRIPTION OF THE INVENTION

Illustrative examples of the active ingredient in the agents of this invention include acrylic acid, vinylacetic acid, vinylpropionic acid, 10-undecylenic acid, 11-dodecenoic acid, 12-tridecenoic acid, 7-nonadecenoic acid, 8-eicoisenoic acid and decicebiuc acid, as well as lower alkyl esters such as methyl and ethyl esters thereof.

The agents of this invention are used in a suitable form such as cream, lotion, emulsion, ointment and liniment.

Agents for preventing the formation of gray hairs of this invention contain unsaturated fatty acids or esters thereof shown by general formula () as the active ingredient in an amount of 0.01 to 10% by weight, preferably 0.5 to 2.0% by weight.

The agents of this invention are substances of high safety that cause no injury to the skin.

As is apparent from the forementioned, this invention provides new agents which ar highly effective in preventing hair from turning gray with no adverse effects upon the skin and hair, and is therefore of great utility.

The following Examples and Test Example will further illustrate the invention.

Example 1 (Treatment oil)

To 20.0 g jojoba oil, 20.0 g mink oil, 1.0 10-undecylenic acid and a trace of perfume, was added squalane to make up a total weight of 100 g, and the mixture was stirred well and put in a container.

Example 2 (Hair cream)

A mixture of 2.0 g polyoxyethylene behenyl ether (20 E.0.), 1.0 g polyoxyethylene-sorbitol tetraoleate (40 E.0.), 2.0 g lipophilic glycerol monostearate, 3.0 g bleached beeswax, 5.0 g microcrystalline wax, 1.3 g behenyl alcohol, 20.0 g liquid paraffin, 10.0 g cetyl octanoate, 1.0 g 10-undecylenic acid and 0.1 butyl p-oxybenzoate was heated until clear to make Solution A.

Separately, a mixture of 0.1 g methyl p-oxybenzoate, 5.0 g 1,3-butylene glycol and 50.5 g pure water was heated until clear to make Solution B.

Solution B was added to Solution A and cooled after stirring to be emulsified. A trace of perfume was then added, and the mixture was stirred well, cooled and put in a container.

Example 3 (Hair cream)

A mixture of 2.0 g polyoxyethylene behenyl ether (20 E.O.), 1.0 g polyoxyethylene-sorbitol tetraoleate (40 E.O.), 2.0 g lipophilic glycerol monostearate, 3.0 g bleached beeswax, 5.0 g microcrystalline wax, 1.3 g behenyl alcohol, 20.0 g liquid paraffin, 10.0 g cetyl octanoate, 1.0 g methyl 7-nonadecenoate and 0.1 g butyl p-oxybenzoate was heated until clear to make Solution A.

Separately, a mixture of 0.1 butyl p-oxybenzoate, 5.0 g 1,3-butylene glycol and 50.5 g pure water was heated until clear to make Solution B.

Solution B was added to Solution A and mixed with stirring, and then the mixture was cooled and put in a container.

Example 4 (Hair tonic)

A mixture of 1.0 g polyoxyethylene adduct of hardened castor oil (60 E.O.), 1.0 g ginger tincture, 0.05 g isopropylmethylphenol, a trace of perfume, 55.0 g ethanol, 1.0 g 10-undecylenic acid and 41.93 g pure water was stirred well, and the homogeneous solution thus obtained was put in a container.

Example 5 (Hair tonic)

A mixture of 1.0 g polyoxyethylene adduct of hardened castor oil (60 E.O.), 1.0 g ginger tincture, 0.05 g isopropyl-methylphenol, a trace of perfume, 55.0 g ethanol, 1.0 g platonin and 41.93 g pure water was stirred well, and the homogeneous solution thus obtained was put in a container.

Test Example (1) Test on melanin formation by B16 cells

[A]

(a) Test method

B16 cells ($4 \times 10^4$) derived from mouse melanoma were suspended in Eagle's MEM containing 10 ml of 10% fetal bovine serum, and the suspension thus obtained was put in a 25 cm$^2$ culture flask and incubated at 37° C. in the presence of 5% $CO_2$. The medium was replaced with a fresh medium containing 40 μmol/1 l of test sample after 0 and 3 days, and incubation was continued for five days. After washing with a phosphate buffer containing 0.8% (w/v) NaCl (pH 7.2), the grown cells were isolated by the use of a solution containing trypsin and EDTA, and recovered by filtration. The cells collected on the filter paper were dried, and the reflected light was measured at 500 nm to determine the reflection absorbance (degree of blackness).

(b) Test samples
(1) Acrylic acid (No. 1)
(2) Vinylacetic acid (No. 2)
(3) Vinylpropionic acid (No. 3)
(4) 10-Undecyclenic acid (No. 4)
(5) Methyl 10-undecylenate (No. 5)
(6) 11-Dodecenoic acid (No. 6)
(7) 12-Tridecenoic acid (No. 7)
(8) 16-Octadecenoic acid (No. 8)
(9) 8-Eicosenoic acid (No. 9)
(10) Decocenoic acid (No. 10)

(c) Test results
The results are shown in Table 1.

TABLE 1

| Sample No. | Amt. of melanin formed (μg/10$^6$ cell) | Rate of increase in amt. based on "control" |
|---|---|---|
| 1 | 7.3 | 1.2 |
| 2 | 6.7 | 1.1 |
| 3 | 6.5 | 1.1 |
| 4 | 13.2 | 2.2 |
| 5 | 13.2 | 2.2 |
| 6 | 9.7 | 1.6 |
| 7 | 15.4 | 2.5 |
| 8 | 10.5 | 1.7 |
| 9 | 8.1 | 1.3 |
| 10 | 7.2 | 1.2 |
| control | 6.1 | 1.0 |

[B]

(a) Test Method 16 melanoma cells ($4 \times 10^5$) derived from mouse melanoma were suspended in Eagle's MEM containing 10 ml of 10% fetal bovine serum, and the suspension thus obtained was put in a 25 cm$^2$ culture flask and incubated at 37° C. in the presence of 5% $CO_2$.

The medium was replaced with a fresh medium which contains 40 μmol/1 l or 60 μmol/1 l of test sample after 0 and 3 days, and incubation was continued for five days.

After washing with a phosphate buffer containing 0.8% (w/v) NaCl (pH 7.2), the grown cells were isolated by the use of a solution containing trypsin and EDTA, and recovered by filtration. The amount of melanin in the cells collected on the filter paper was measured.

(b) Test Samples
(1) 7-Nonadecenoic acid (No. 1)
(2) 8-Eicosenoic acid (No. 2)

(c) Test results
The results are shown in Table 2.

TABLE 2

| Sample No. | Amt. of test sample added(μM) | Amt. of melanin formed (μg/10$^6$cell) |
|---|---|---|
| 1 | 40 | 2.74(172%) |
|   | 60 | 3.20(201%) |
| 2 | 40 | 1.93(121%) |
|   | 60 | 3.53(222%) |
| control | 0 | 1.59(100%) |

(2) Test of preventing gray hair formation on people (a) Test method

This test was made on ten people (seven men and three women) from 35 to 60 years old having gray hairs. Each of the test agents was embrocated on the head skin twice a day (in the morning and evening) in an amount of about 1.5 ml each, and the number of gray hairs included in 1000 hairs on the top of head was counted before application of the agent and after six months.

(b) Agents tested
(1)
  10-Undecylenic acid: 1%
  95% Ethanol: 50%
  Glycerol: 5%
  Pure water: 44%
(2)
  7-Nonadecenoic acid: 1%
  95% Ethanol: 50%
  Glycerol: 5%
  Pure water: 44%

(3)
  8-Eicosenoic acid: 1%
  95% Ethanol: 50%
  Glycerol: 5%
  Pure water: 44%
  (% herein means weight %)
(c) Test results The results are shown in Table 3.

As can be seen from the table, the agents of this invention activate the formation of melanin which is the key substance for the growth of black hair, and are highly effective in preventing human hair from turning gray.

TABLE 3

| | Number of gray hairs | | | | | |
|---|---|---|---|---|---|---|
| | Sample 1 | | Sample 2 | | Sample 3 | |
| Subject No. | Before application | After 6 months | Before application | After 6 months | Before application | After 6 months |
| 1 | 93 | 77 | 193 | 182 | 156 | 143 |
| 2 | 96 | 49 | 401 | 289 | 151 | 98 |
| 3 | 45 | 37 | 50 | 45 | 108 | 91 |
| 4 | 56 | 48 | 203 | 200 | 40 | 40 |
| 5 | 156 | 147 | 81 | 80 | 283 | 113 |
| 6 | 84 | 81 | 274 | 114 | 92 | 88 |
| 7 | 222 | 166 | 32 | 25 | 211 | 55 |
| 8 | 70 | 67 | 111 | 88 | 87 | 47 |
| 9 | 12 | 10 | 142 | 121 | 95 | 51 |
| 10 | 137 | 98 | 29 | 15 | 67 | 65 |

What is claimed is:

1. A method of preventing the formation of gray hair comprising applying to the skin of a person's head an agent containing, as an active ingredient, an unsaturated fatty acid or an ester thereof represented by the following general formula:

$$A-COOR$$

wherein A is a radical of $CH_2=CH(CH_2)_n-$ or $CH_3(CH_2)_{10}CH=CH-(CH_2)_m-$, R is a hydrogen atom or alkyl group having 1 or 2 carbon atoms, n is an integer from 0 to 22, and m is an integer of 5 or 6.

2. A method as in claim 2, wherein said unsaturated fatty acid or ester thereof is selected from the group consisting of acrylic acid, vinylacetic acid, vinylpropionic acid, 10-undecylenic acid, 11-dodecenoic acid, 12-tridecenoic acid, 7-nonadecenoic acid, 16-octadecenoic acid, 8-eicoisenoic acid, decocenoic acid, and methyl and ethyl esters thereof.

3. A method as in claim 1, wherein said unsaturated fatty acid or ester thereof is present in an amount ranging from 0.01 to 10% by weight of the agent.

4. A method as in claim 1, wherein said unsaturated fatty acid or ester thereof is present in an amount ranging from 0.5 to 2% by weight of the agent.

5. A method as in claim 1, wherein said agent is selected from the group consisting of a cream, lotion, emulsion, ointment and lintment.

* * * * *